US011460434B2

(12) United States Patent
Wang et al.

(10) Patent No.: US 11,460,434 B2
(45) Date of Patent: Oct. 4, 2022

(54) GAS DETECTION SYSTEM WITH ELIMINATING INFLUENCE OF AMBIENT TEMPERATURE AND HUMIDITY CHANGES AND THE METHOD THEREOF

(71) Applicant: SAPIENS ENVIRONMENTAL TECHNOLOGY CO., LTD., Guangdong (CN)

(72) Inventors: Ying Wang, Guangdong (CN); Li Sun, Guangdong (CN); Qing Zhang, Guangdong (CN); Zhi Ning, Guangdong (CN)

(73) Assignee: SAPIENS ENVIRONMENTAL TECHNOLOGY CO., LTD., Shenzhen (CN)

( * ) Notice: Subject to any disclaimer, the term of this patent is extended or adjusted under 35 U.S.C. 154(b) by 166 days.

(21) Appl. No.: 16/968,278

(22) PCT Filed: May 29, 2019

(86) PCT No.: PCT/CN2019/088916
§ 371 (c)(1),
(2) Date: Aug. 7, 2020

(87) PCT Pub. No.: WO2020/237513
PCT Pub. Date: Dec. 3, 2020

(65) Prior Publication Data
US 2021/0310986 A1   Oct. 7, 2021

(51) Int. Cl.
*G01N 27/417* (2006.01)
*G01N 33/00* (2006.01)
(Continued)

(52) U.S. Cl.
CPC ......... *G01N 27/4175* (2013.01); *G01N 1/405* (2013.01); *G01N 7/10* (2013.01);
(Continued)

(58) Field of Classification Search
CPC ........... G01N 27/4175; G01N 33/0006; G01N 21/3504; G01N 27/64; G01N 7/10; G01N 33/0011; G01N 33/0047; G01N 2001/4016
(Continued)

(56) References Cited

U.S. PATENT DOCUMENTS

2006/0173637 A1* 8/2006 Martin ............... G01N 33/0006
702/24
2010/0063748 A1* 3/2010 Mottier .............. G01N 21/3504
702/24
(Continued)

FOREIGN PATENT DOCUMENTS

CN         106770523 A      5/2017
WO    WO-2021184130 A1 *  9/2021

*Primary Examiner* — Clayton E. LaBalle
*Assistant Examiner* — Kevin C Butler

(57) ABSTRACT

The invention provides a gas detection system and a method with eliminating influence of ambient temperature and humidity change, the gas detection system comprises a bare sensor, a reference sensor and a calculation module; the bare sensor is used to detect a target gas in an ambient gas to obtain a first feedback signal; the reference sensor is used to selectively isolate the target gas in the ambient gas to produce a zero gas and to detect the zero gas to obtain a second feedback signal, the calculation module is used to calculate a difference between the first feedback signal and the second feedback signal to obtain a third feedback signal, and to obtain a target gas concentration by calculating the third feedback signal according to a calibration formula. The invention improves the measurement accuracy to the target gas concentration, which are efficient and reliable and have good technical effects.

20 Claims, 12 Drawing Sheets

(51) Int. Cl.
  *G01N 7/10*        (2006.01)
  *G01N 1/40*        (2006.01)
  *G01N 21/3504*     (2014.01)
  *G01N 27/64*       (2006.01)

(52) U.S. Cl.
  CPC ..... *G01N 33/0006* (2013.01); *G01N 33/0011* (2013.01); *G01N 33/0047* (2013.01); *G01N 21/3504* (2013.01); *G01N 27/64* (2013.01); *G01N 2001/4016* (2013.01)

(58) Field of Classification Search
  USPC ....................................................... 73/31.07
  See application file for complete search history.

(56) References Cited

U.S. PATENT DOCUMENTS

2021/0310986 A1* 10/2021 Wang ................ G01N 33/0006
2022/0042903 A1*  2/2022 Sagberg ............ G01N 33/0029

* cited by examiner

GAS DETECTION SYSTEM WITH ELIMINATING INFLUENCE OF AMBIENT TEMPERATURE AND HUMIDITY CHANGES AND THE METHOD THEREOF

TECHNICAL FIELD

The invention relates to the technical field of gas detection, and more specifically, relates to a gas detection system and its method with eliminating the influence of ambient temperature and humidity changes.

BACKGROUND

The gas sensors are becoming a new type of air pollutant monitoring technology which is different from traditional monitoring methods due to the characteristics of their low price, small size, easy integration, and easy distribution. Environmental monitoring methods based on gas sensors have also been gradually applied to different scenes, such as the environmental atmosphere monitoring, grid monitoring, industrial monitoring, etc. According to the different principles of the gas sensors, they are mainly divided into electrochemical sensors, metal oxide sensors, photoionization sensors, and non-dispersive infrared sensors and so on. The researches have shown that the output signal of the gas sensor is not only affected by the change of the target pollutant concentration, but also by the change of temperature and humidity of the ambient during the testing and monitoring of most gas sensors. This kind of influence caused by temperature and humidity will change the monitoring baseline and sensitivity of target pollutants, thus causing the measurement errors in the sensor in ambient applications. At the same time, the physical and chemical structure of the sensor itself will change with the increase of application time, which will cause the problem of signal offset.

At present, in order to improve the accuracy of monitoring in the environmental monitoring application of gas sensors, the mathematical algorithms are usually used to compensate for the temperature and humidity of the ambient, or to carry out pre-treatment of the sampled gas which include a series of temperature control or humidity control, in order to improve the stability and predictability of the relationship between the sensor output signal and the target pollutant. Some sensor integrators use the method of filtering to separate the target signal from the interference pollutant signal in order to remove the effects of interference pollutants in the interference removal of cross-environmental pollutants.

However, in the current technological development, these methods cannot effectively separate the sensor output signal in the target gas pollutant concentration signal and ambient temperature and humidity influence signal. Mathematical algorithms, including linear fit, nonlinear fitting, segmentation functions, machine learning, and neuron networks, also cannot accurately capture the delay, nonlinear and cross-effects of the impact of ambient temperature and humidity on the sensor. Moreover, the short-term drastic and long-term chronic impacts of humidity changes on the sensor are still not effectively described by mathematical models. At the same time, the physical pretreatment of gases also greatly increases the complexity, volume and power consumption of the sensor systems. Whether it is temperature control or humidity control, it is impossible to control two ambient variables at the same time, even through the proportional-integral derivative-algorithm to quickly control of temperature or humidity, the small fluctuating signal in the process will also produce amplification effect on the sensor signal, thus artificially producing a large noise and negatively affecting the accuracy of detection.

SUMMARY

In view of the problem of how to effectively separate the pollutant concentration signal and the influence signal of ambient temperature and humidity from the sensor output signal. The present invention provides a gas detection system and method with eliminating the influence of ambient temperature and humidity changes on the gas sensor reference output signal, and make the gas sensor which is easy to be affected by the ambient temperature and humidity is free from the influence of the temperature and humidity changes on the gas sensor reference output signal in the environment detection, and then improves the measurement accuracy and stability of the gas sensor under all-weather conditions.

To solve the drawbacks in prior art, the technical solutions to solve the technical problem are as follows:

In one aspect, a gas detection system is provided with eliminating the effects of changes in ambient temperature and humidity, comprising: a bare sensor used to detect a target gas in an ambient gas to obtain a first feedback signal; a reference sensor used to selectively isolate the target gas in the ambient gas to generate a zero gas, and to detect the zero gas to obtain a second feedback signal; and a calculation module connected to the bare sensor and reference sensor being used to calculate a difference between the first feedback signal and the second feedback signal to obtain a third feedback signal, and to obtain a target gas concentration by calculating the third feedback signal according to a calibration formula.

In one embodiment of the present invention, the reference sensor comprises a sensor body having a consistent signal response to the target gas and ambient temperature and humidity with the bare sensor; and a target gas selective isolation layer having heat conduction and water vapor exchange function for selectively isolating the target gas in the ambient gas to generate the zero gas.

wherein the calibration formula is: $C=a*V3+b$; C is the target gas concentration, the unit of the target gas concentration is mass concentration or mixing ratio; V3 is the third feedback signal, the unit of the third feedback signal is consistent with output signal of the bare sensor and sensor body; and a and b are calibrated parameters.

In this embodiment of the present invention, the first feedback signal, the second feedback signal and the third feedback signal include any one of voltage value, current value and concentration value.

In this embodiment of the present invention, the difference between the first feedback signal and the second feedback signal includes a direct signal difference between the first feedback signal and the second feedback signal and a correction signal difference after proportional correction between the first feedback signal and the second feedback signal.

In some preferred embodiments of the present invention, the gas detection system further comprises a sensor seat equipped with a sampling gas chamber communicated with the ambient gas, and the bare sensor and sensor body are installed in the sensor seat respectively.

In this preferred embodiment of the present invention, the sensor seat is provided with a first accommodating cavity and a second accommodating cavity on both sides of the sampling gas chamber, a first sensor protective film is arranged between the sampling gas chamber and the first accommodating cavity, a second sensor protective film is arranged between the sampling gas chamber and the second accommodating cavity, the first accommodating cavity is used to install the bare sensor, and the second accommodating cavity is used to install the sensor body. The target gas selective isolation layer is wrapped on one side of the second sensor protective film, and the side is facing the sampling gas chamber.

In this preferred embodiment of the present invention, the number of sensor bodies is a plurality, and the plurality of sensor bodies are installed in the second accommodating cavity. The target gas selective isolation layer is covered on reaction surface of the sensor body without gaps.

In other preferred embodiment of the present invention, the gas detection system further comprises a first sensor seat and a second sensor seat which are respectively equipped with a first sampling gas chamber and a second sampling gas chamber communicated with the ambient gas, the bare sensor is installed in the first sampling gas chamber, the sensor body is installed in the second sampling gas chamber. The target gas selective isolation layer is covered on surface of the second sampling gas chamber.

In other preferred embodiment of the present invention, the number of sensor bodies is a plurality, and the plurality of sensor bodies are installed in the second sampling gas chamber. The target gas selective isolation layer is covered on reaction surface of the sensor body without gaps.

In some embodiments of the present invention, the gas detection system further comprises a sampling gas path connected a sensor seat, the sampling gas path includes a passive diffusion type gas sampling gas path and an active pumping type sampling gas path; wherein the active pumping type sampling gas path includes an gas inlet pipe and an gas extraction pump, the gas inlet pipe is arranged on the sensor seat and communicated with a sampling gas chamber, and the gas extraction pump is communicated with the gas inlet pipe.

In one embodiment of the present invention, the bare sensor and sensor body comprise any one of electrochemical sensor, metal oxide sensor, photoionization sensor and non dispersive infrared sensor.

In one embodiment of the present invention, the target gas selective isolation layer includes any one of filter paper, filter membrane, molecular sieve, filter device and a covering structures formed by selective filter material filling.

In one embodiment of the present invention, the sensor body is an electrochemical sensor, the target gas selective isolation layer is arranged on surface of internal electrolyte layer of the electrochemical sensor.

Another aspect of the present invention provides a gas detection method with eliminating influence of ambient temperature and humidity change, wherein the gas detection method comprising: obtaining a first feedback signal by detecting a target gas in an ambient gas with a bare sensor; obtaining a second feedback signal by selectively isolating the target gas in the ambient gas to generate a zero gas and detecting the zero gas with a reference sensor; and calculating a difference between the first feedback signal and the second feedback signal to obtain a third feedback signal, and obtaining a target gas concentration by calculating the third feedback signal according to a calibration formula.

When implementing the gas detection system of the present invention, the following advantageous effects can be achieved:

A gas detection system and a method with eliminating the influence of changes in ambient temperature and humidity are provided by the present invention, the target gas concentration is obtained by calculating the signal difference between the bare sensor and the reference sensor, the gas detection system can be used for effectively separating the target gas concentration signal and the ambient temperature and humidity signal from the sensor output signal, eliminating the influence of the change of ambient temperature and humidity on the sensor output signal, and improving the measurement accuracy, and measurement stability to the target gas concentration.

BRIEF DESCRIPTION OF THE DRAWINGS

The present invention will be further described with reference to the accompanying drawings and embodiments in the following, in the accompanying drawings.

DETAILED DESCRIPTION OF THE PREFERRED EMBODIMENT

In order to enable those skilled in the art to understand the present invention more clearly, the present invention will be described in further detail with reference to the accompanying drawings and specific embodiments.

In order to effectively separate the atmospheric pollutant concentration signal and the ambient temperature and humidity signal from the sensor output signal, to eliminate the influence of ambient temperature and humidity changes on the detection of atmospheric pollutant concentration, and then improve the measurement accuracy and precision of the gas sensor, the present invention provides a gas detection system and method with eliminating the influence of ambient temperature and humidity changes. The core idea is that provide a packaging method of a bare sensor and a reference sensor. The bare sensor is configured for detecting the target gas in the ambient gas to obtain a first feedback signal. The reference sensor is configured for isolating the target gas in the ambient gas, detecting the zero gas to obtain a second feedback signal, and obtaining a third feedback signal by calculating the difference value between the first feedback signal and the second feedback signal, and then obtaining the target gas concentration by calculating the third feedback signal according to a calibration formula. The target gas concentration value effectively separates the influence of changes in the ambient temperature and humidity, and improves the monitoring accuracy, and stability of the target gas.

Figure 1:
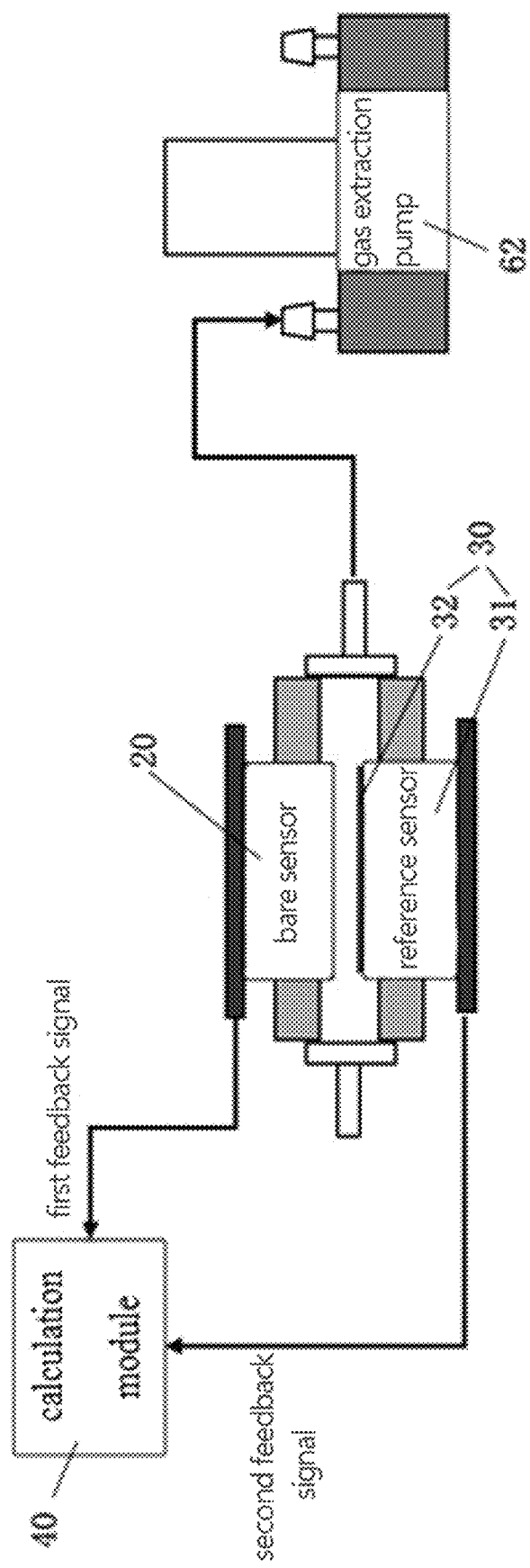
FIG. 1 is a schematic view of the gas detection system according to the first embodiment of the present invention.

As shown in FIG. 1, the gas detection system provided in the first embodiment of the present invention includes a bare sensor 20, a reference sensor 30, and a calculation module 40. The bare sensor 20 is configured for detecting a target gas in the ambient gas to obtain a first feedback signal, and the reference sensor 30 configured for selectively isolating the target gas in the ambient gas to generate the zero gas, and detecting the zero gas to obtain a second feedback signal, the calculation module 40 is connected to the bare sensor 20 and the reference sensor 30, which is configured for calculating a difference value between the first feedback signal and the second feedback signal to obtain a third feedback signal, and then to calculate and obtain the target gas concentration by calculating the third feedback signal according to a calibration formula.

The reference sensor 30 includes a sensor body 31 and a target gas selective isolation layer 32. The sensor body 31 and the bare sensor 20 have a consistent signal response to the target gas and ambient temperature and humidity. That is, the sensor body 31 and the bare sensor 20 are same type sensors with consistent response characteristics to the ambient temperature; the target gas selective isolation layer 32 has heat conduction and water vapor exchange functions for selectively isolating the target gas in the ambient gas to generate zero gas in order to ensure that the bare sensor 20 and the reference sensor 30 have a consistent response to the signals of ambient temperature and humidity changes.

Further, the calibration formula is: $C=a*V3+b$; where C is the target gas concentration, the unit of the target gas concentration is mass concentration or mixing ratio, V3 is the third feedback signal, the unit of the third feedback signal is consistent with output signal of the bare sensor 20 and sensor body 31, and a and b are calibrated parameters. Wherein, the first feedback signal, the second feedback signal and the third feedback signal include any one of voltage value, current value and concentration value; the difference value between the first feedback signal and the second feedback signal includes a direct signal difference value between the first feedback signal and the second feedback signal and a correction signal difference value after proportional correction between the first feedback signal and the second feedback signal.

It should be noted that the effective reaction surface of the sensor body 31 is completely covered by the target gas selective isolation layer 32, so that the sensor body 31 is only affected by the temperature and humidity in the ambient gas, which is not affected by the target gas concentration change. The reaction surface of the bare sensor 20 is completely in contact with the ambient gas, the bare sensor 20 is simultaneously affected by the target gas concentration and changes in temperature and humidity in the ambient gas during the operation of the sensor.

Therefore, the first feedback signal is a signal feedback that is comprehensively affected by the concentration of the target gas and the temperature and humidity of the ambient where it is located, and the second feedback signal is comprehensively affected by the zero gas produced by the isolation of the target gas and the ambient temperature and humidity. The third feedback signal is the signal feedback of the target gas concentration, which removes the influence of the ambient temperature and humidity to the target gas by calculating the difference value between the first feedback signal and the second feedback signal, and contains only the target gas concentration signal feedback from sensors.

Figure 2:
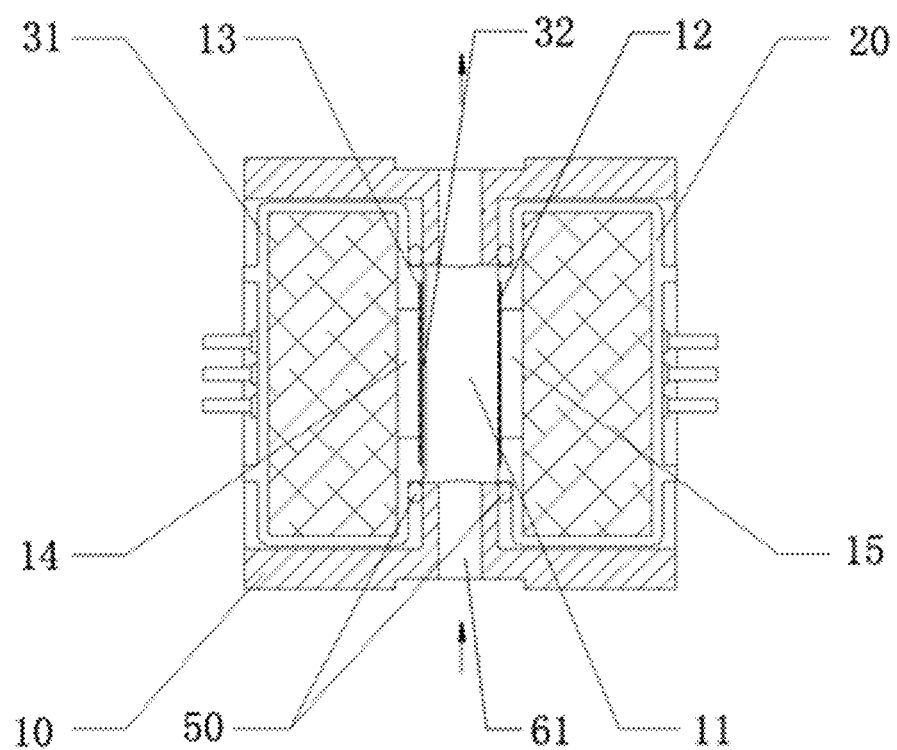
FIG. 2 is a schematic view of an assembly structure of the gas detection system according to the first embodiment of the present invention.

FIG. 2 is a schematic view of an assembly structure of the gas detection system according to the first embodiment of the present invention.

As shown in FIG. 2, the gas detection system further comprises a sensor seat 10, the sensor seat 10 is equipped with a sampling gas chamber 11 communicated with the ambient gas, the bare sensor 20 and the sensor body 31 are respectively installed in the sensor seat 10.

The sensor seat 10 is provided with a first accommodating cavity and a second accommodating cavity on both sides of the sampling gas chamber 11, a first sensor protective film 12 is arranged between the sampling gas chamber 11 and the first accommodating cavity, a second sensor protective film 13 is arranged between the sampling gas chamber 11 and the second accommodating cavity, the first accommodating cavity is used to install the bare sensor 20, and the second accommodating cavity is used to install the sensor body 31.

In this embodiment, the target gas selective isolation layer 32 is wrapped on one side of the second sensor protective film 13, and the side is facing the sampling gas chamber 11; a zero gas chamber 14 is formed between the target gas selective isolation layer 32 and the sensor body 31. A test gas chamber 15 is formed between the first sensor protective film 12 and the bare sensor 20 at intervals.

The number of the sensor bodies 31 may also be set as a plurality, and the plurality sensor bodies 31 are all installed in the second accommodating cavity, which are configured for jointly detecting the zero gas and obtaining the second feedback signal of the array.

Figure 3:
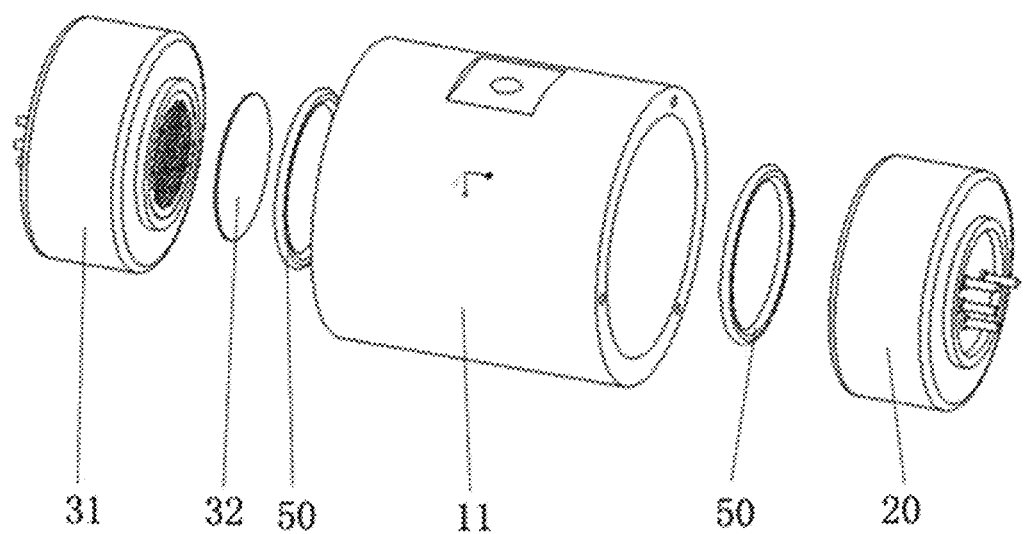
FIG. 3 is another schematic view of the assembly structure of the gas detection system according to the first embodiment of the present invention.

FIG. 3 is another assembly schematic view of the gas detection system provided by the first embodiment of the present invention. Referring to FIG. 3, the target gas selective isolation layer 32 is covered on the reaction surface of the sensor body 31 without gaps, the target gas selective isolation layer 32 can also isolates the target gas in the ambient gas to generate zero gas. The structure of the present invention is simpler and more practical.

Furthermore, seal rings 50 are respectively sleeved at the connection between the bare sensor 20 and the sampling gas chamber 11, and the connection between the sensor body 31 and the sampling gas chamber 11 for sealing the connections to ensure no air leakage.

Furthermore, the gas detection system further includes a sampling gas path connected to the sensor seat 10, the sampling gas path includes a passive diffusion gas sampling gas path and an active pumping sampling gas path; the active pumping sampling gas path includes the gas inlet pipe 61 and the gas extraction pump 62, the gas inlet pipe 61 is arranged on the sensor seat 10 and is communicated with the sampling gas chamber 11, and the gas extraction pump 62 is communicated with the gas inlet pipe 61 for sucking ambient gas into the sampling gas chamber 11 to improve gas detection efficiency. For the passive diffusion-type gas sampling gas circuit can refer to the prior art sensor gas circuit structure, and details are not described in this embodiment.

In this embodiment, the bare sensor 20 and the sensor body 31 include any one of an electrochemical sensor, metal oxidation sensor, photo-ionization sensor, and non-dispersive infrared sensor, and may also be other sensor types affected by ambient temperature and humidity signals;

The target gas selective isolation layer 32 includes any one of filter paper, filter membrane, molecular sieve, filter device, and cover structure formed by selective filter material filling, which can be selected according to actual needs.

Preferably the sensor body 31 is an electrochemical sensor, and the target gas selective isolation layer 32 is provided on the surface of the internal electrolyte layer of the electrochemical sensor, that is, the target gas selective isolation layer 32 is directly placed between the internal electrolyte layer of the electrochemical sensor and the ambient gas, it is used to selectively isolate the target gas in the ambient gas to generate zero gas.

The gas detection system provided in the second embodiment of the present invention, the bare sensor and the reference sensor are respectively installed in two gas chambers with the same structure. Specifically, the gas detection system includes a first sensor seat and a second sensor seat. The first sensor seat and the second sensor seat are respectively equipped with a first sampling gas chamber and a second sampling gas chamber that communicate with the ambient gas. The bare sensor is installed in the first sampling gas chamber and is configured for detecting the target gas in the ambient gas to obtain the first feedback signal; the sensor body is installed in the second sampling gas chamber, which is configured for selectively isolating the target gas in the ambient gas to generate zero gas, and detecting the zero gas to obtain the second feedback signal; similarly, the third feedback signal can be obtained by calculating the difference value between the first feedback signal and the second feedback signal, and the concentration of the target gas can be obtained by calculating the third feedback signal according to the calibration formula.

In the second embodiment of the present invention, the target gas selective isolation layer is also provided in two ways. The first method is to cover the target gas selective isolation layer on the surface of the second sampling gas chamber, so that the second sampling gas chamber becomes a zero gas cell. At this time, the number of the sensor bodies may be set to be a plurality, and the plurality of sensor bodies configured for jointly detecting the zero gas and obtaining the second feedback signal of the array are all installed in the second sampling gas chamber.

The second method is to cover the target gas selective isolation layer on the reaction surface of the sensor body without gaps, and then place the sensor body in the second sampling gas chamber, which can also achieve that the target gas selective isolation layer isolates the target gas in the ambient gas to produce zero gas.

Figure 4:
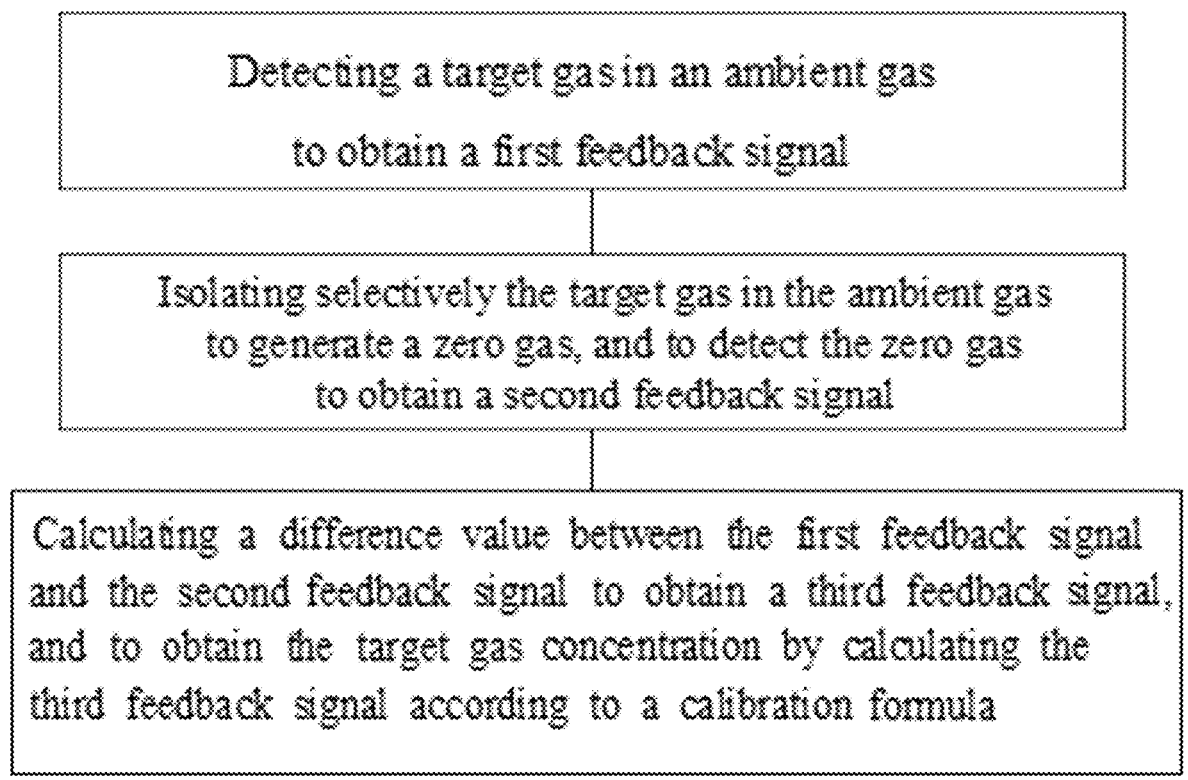
FIG. 4 is a step flowchart of the gas detection method according to third embodiment of the present invention.
Figure 5A:
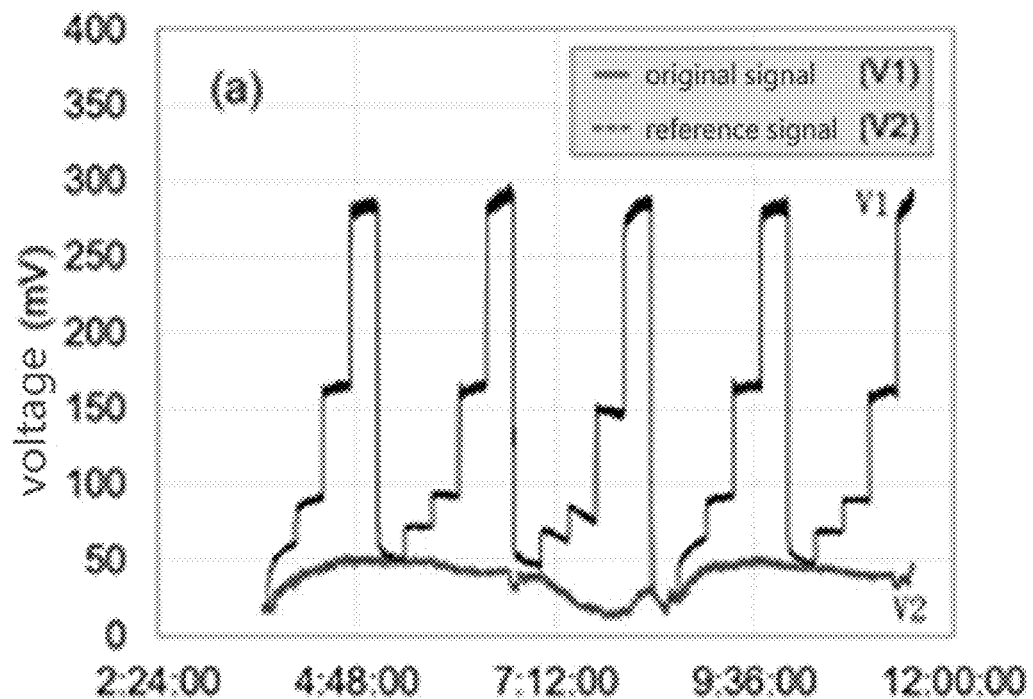
FIGS. 5 (*a*), (*b*), (*c*) and (*d*) are the variation curve of the voltage signal V2 of the covered nitrogen dioxide sensor, the variation curve of the voltage signal V1 of the bare nitrogen dioxide sensor, the variation curve of the temperature and humidity of the standard gas, and the variation curve of the target gas concentration finally obtained through the difference calculation during the sampling process respectively according to the first embodiment of the present invention.
Figure 5B:
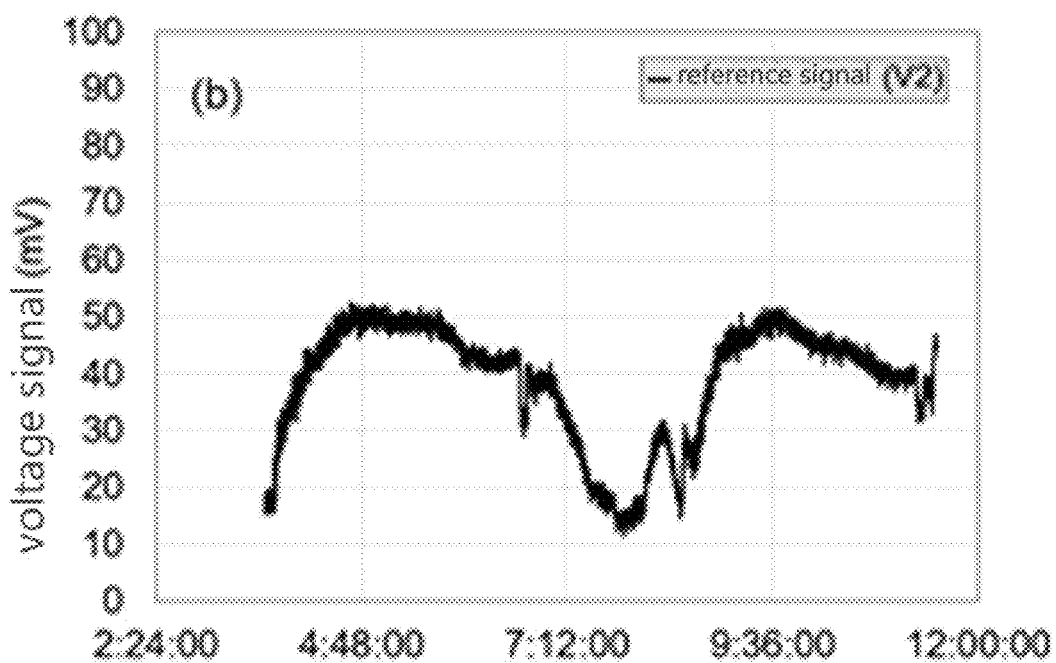
Figure 5C:
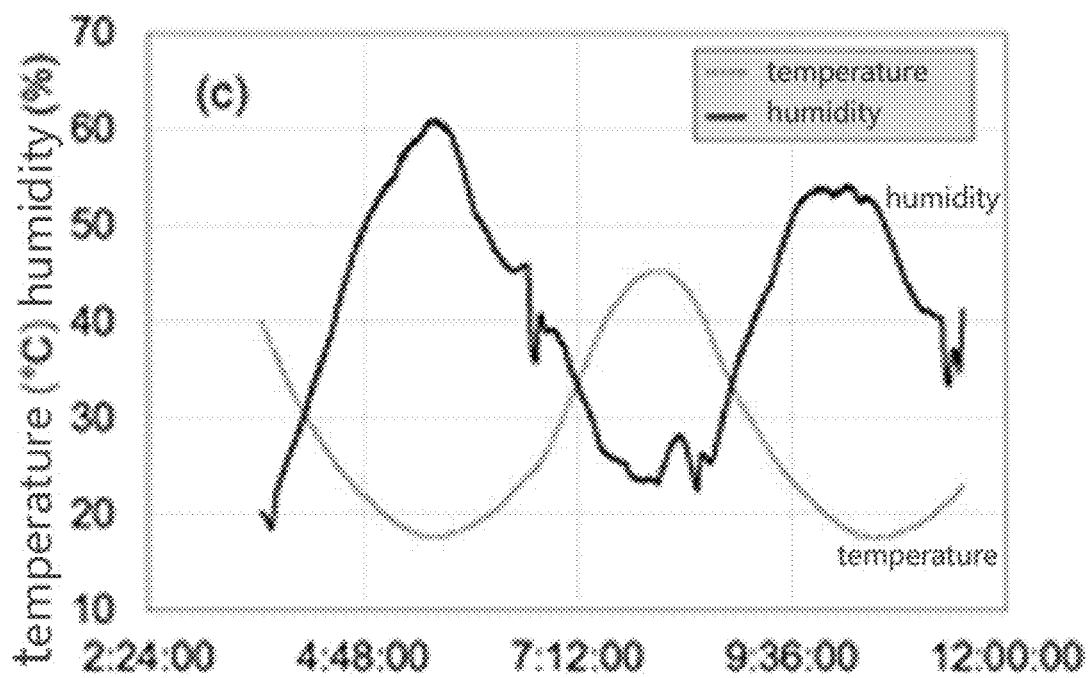
Figure 5D:
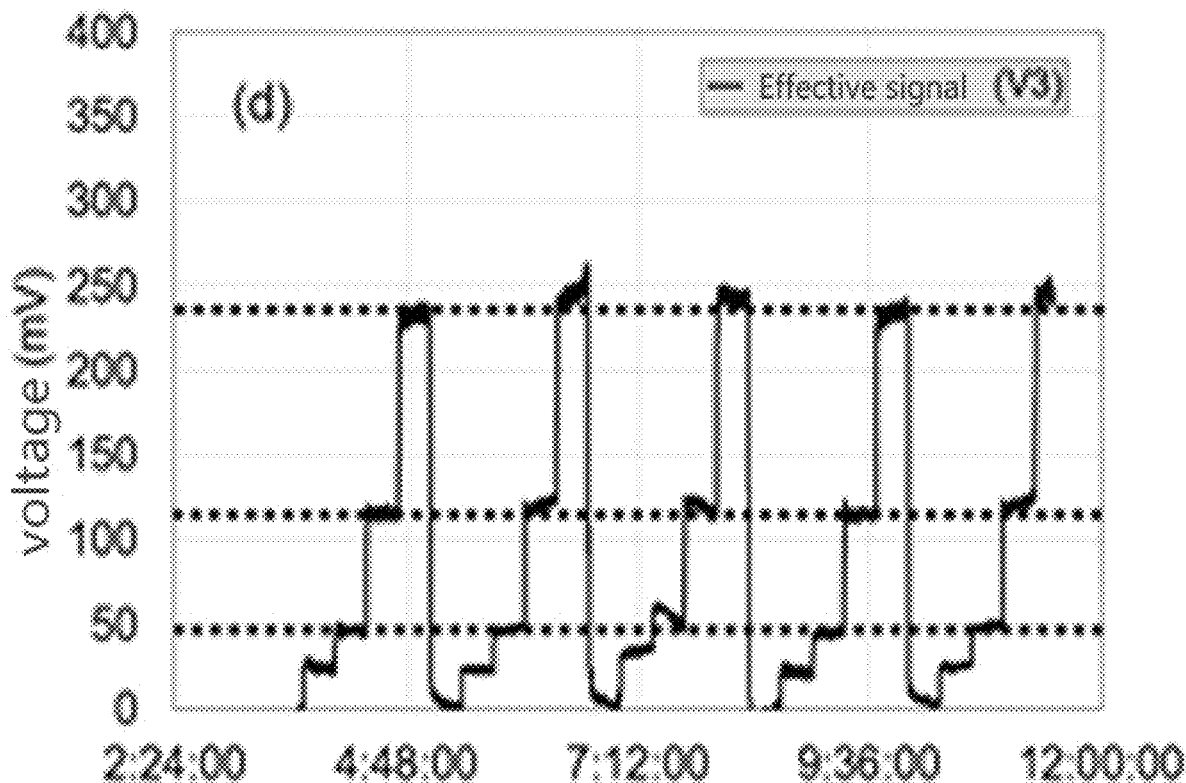
Figure 6A:
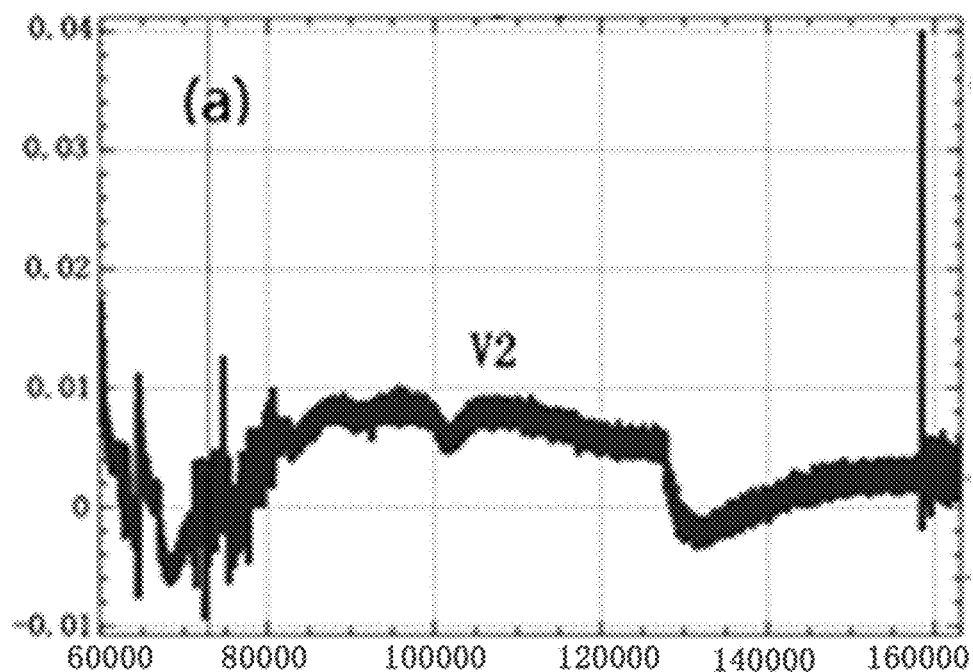
FIGS. 6 (*a*), (*b*), (*c*), and (*d*) are the variation curve of the voltage signal V2 of the covered nitrogen dioxide sensor, the bare nitrogen dioxide sensor, the variation curve of the voltage signal V1, the variation curve of the temperature and humidity of the standard gas, and the variation curve of the target gas concentration finally obtained through the difference calculation during the sampling process respectively p according to the second embodiment of the present invention.
Figure 6B:
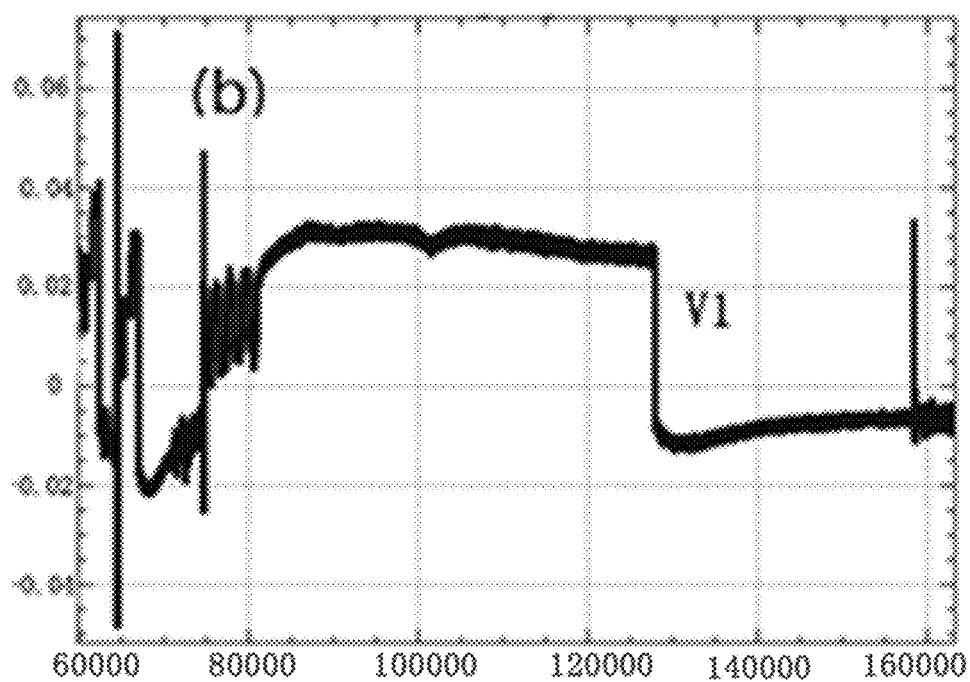
Figure 6C:
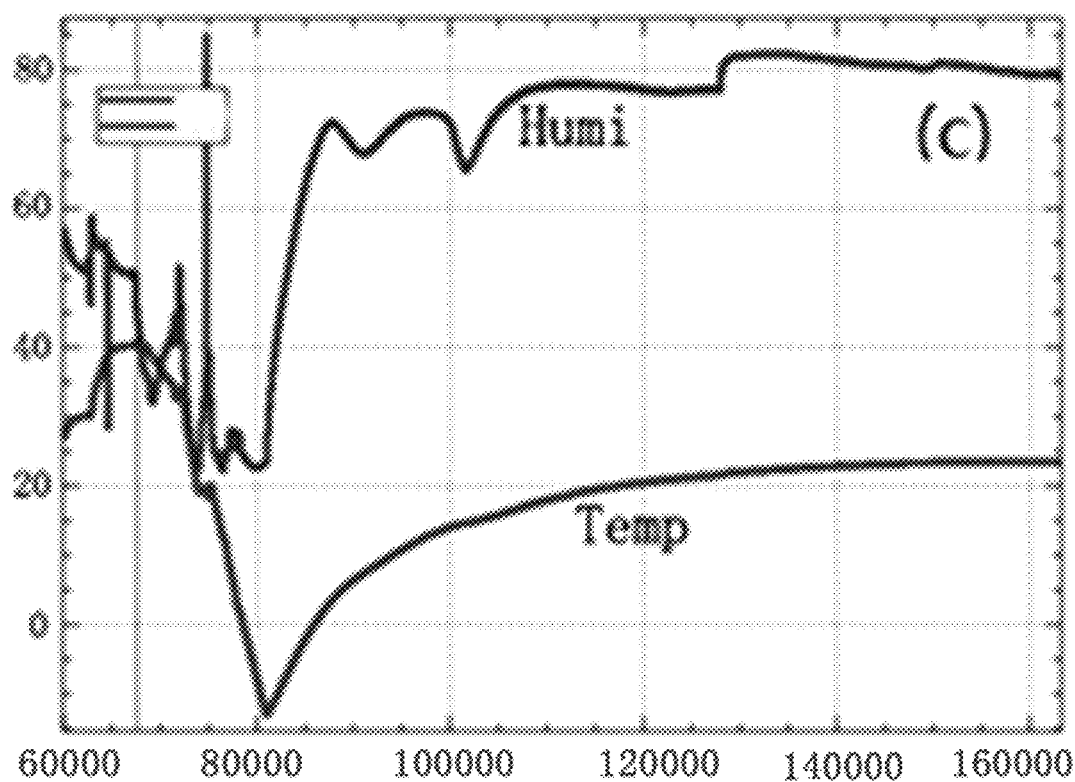
Figure 6D:
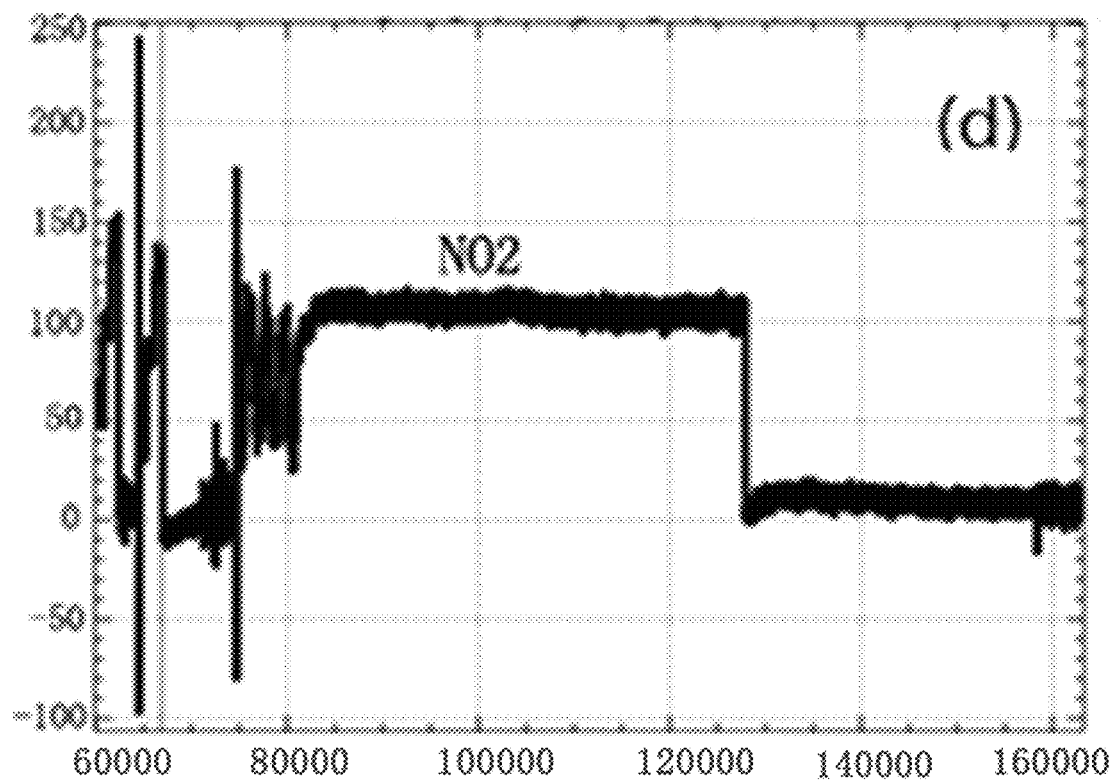
Figure 7A:
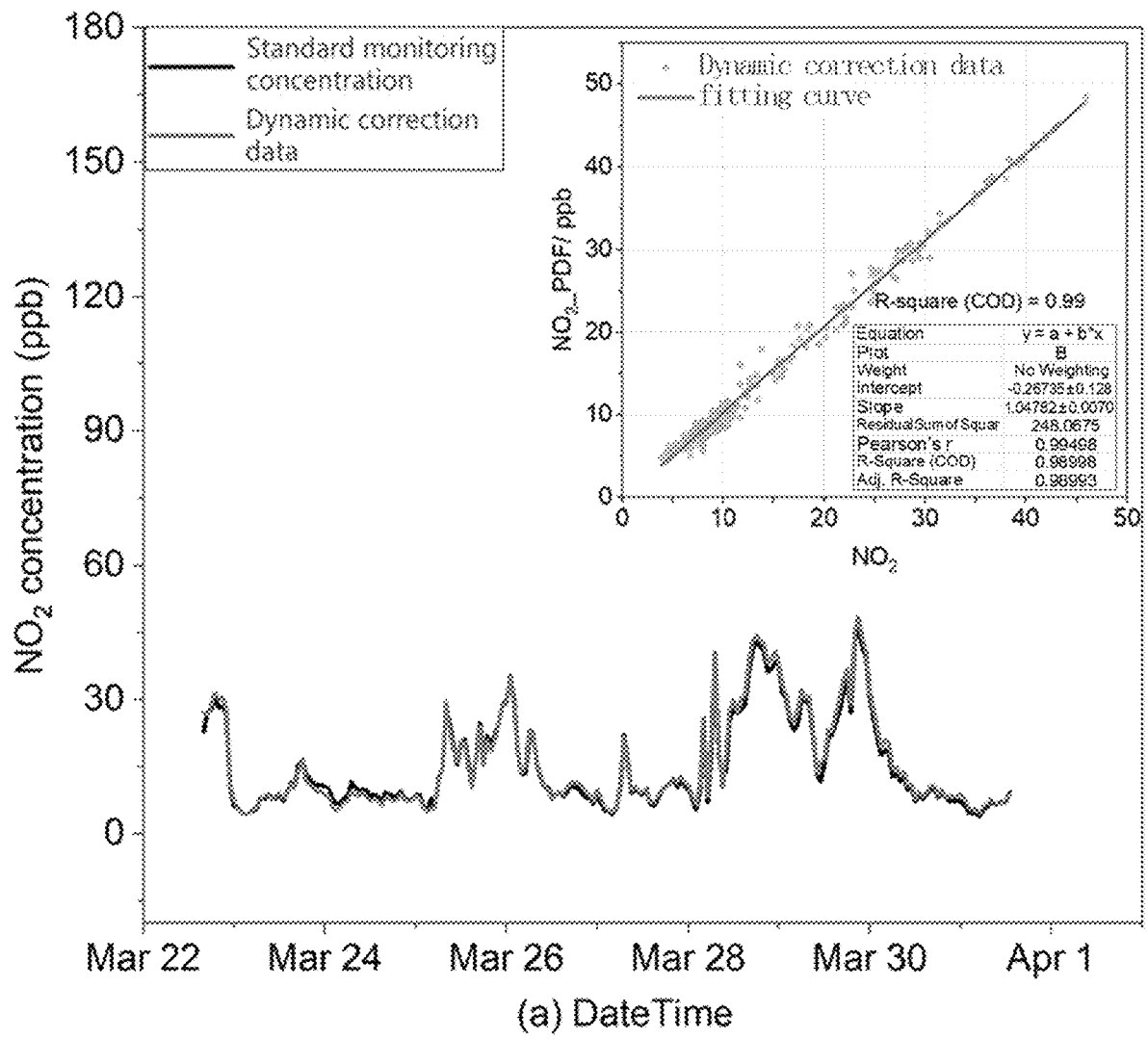
FIGS. 7(*a*), (*b*), (*c*) and (*d*) are the comparison curves between the concentrations of nitrogen dioxide, nitric oxide and ozone pollutants obtained by the gas detection system provided by the present invention and their standard concentrations respectively, and the corresponding ambient temperature and humidity variation curve.
Figure 7B:
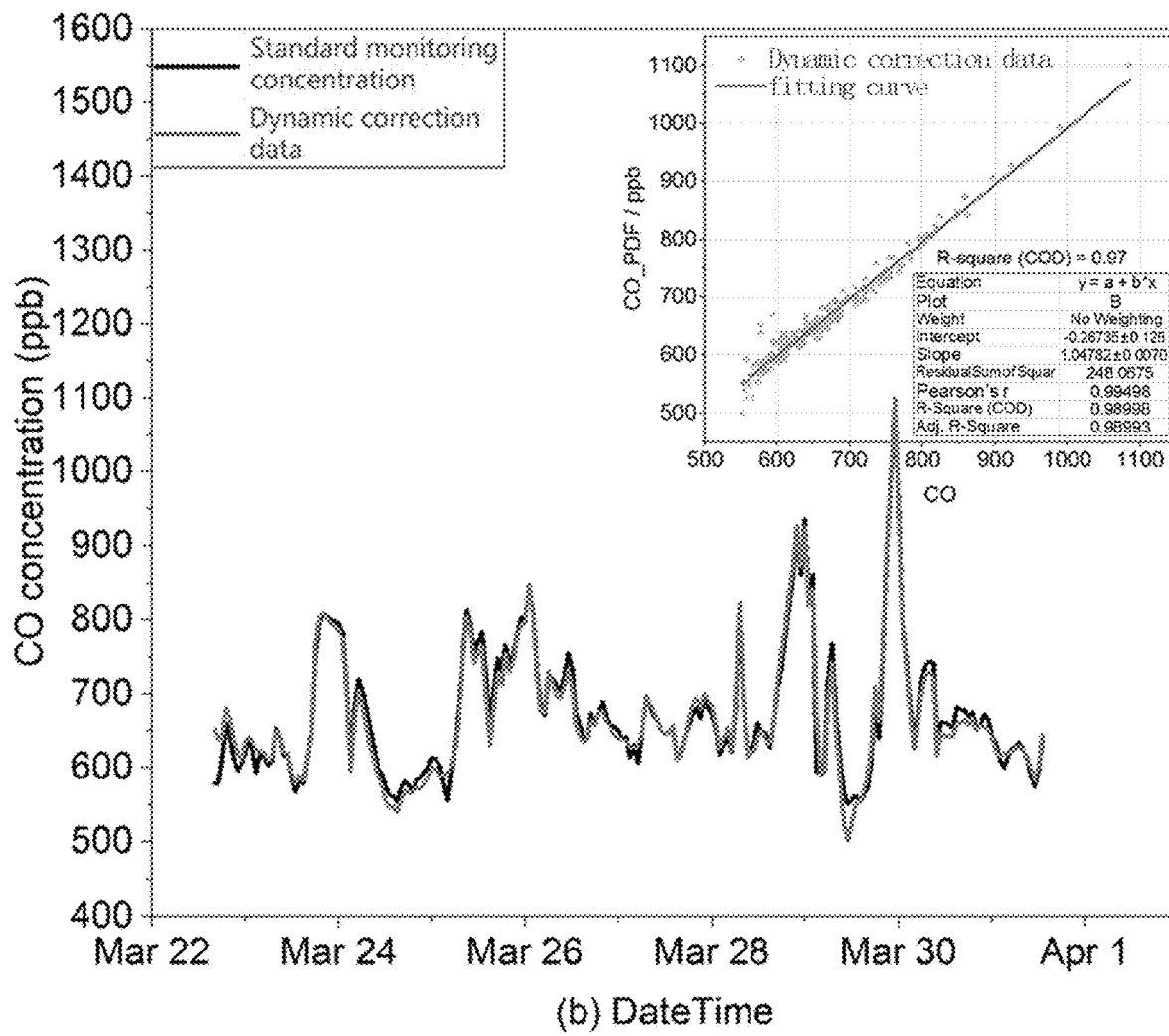
Figure 7C:
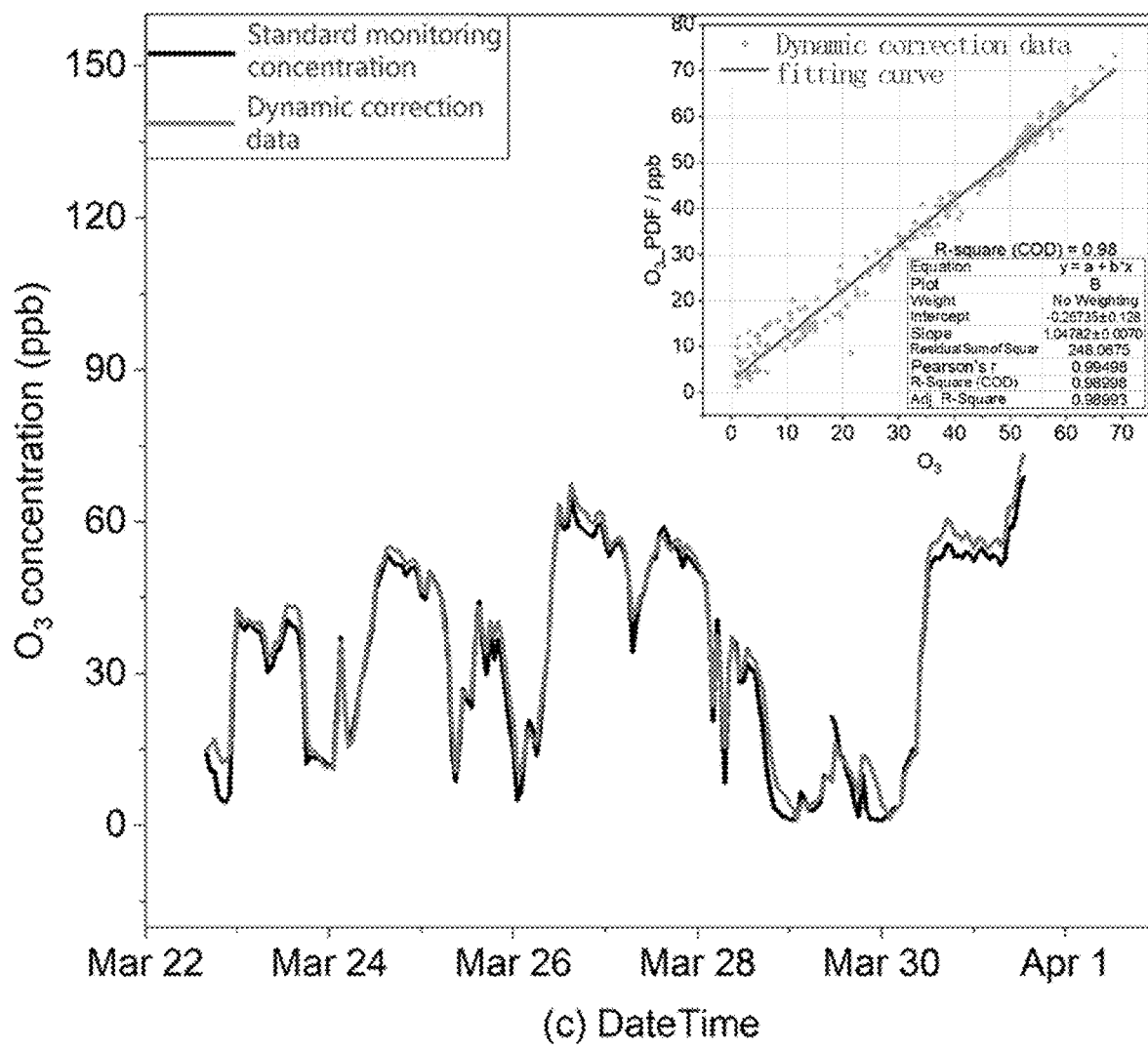
Figure 7D:
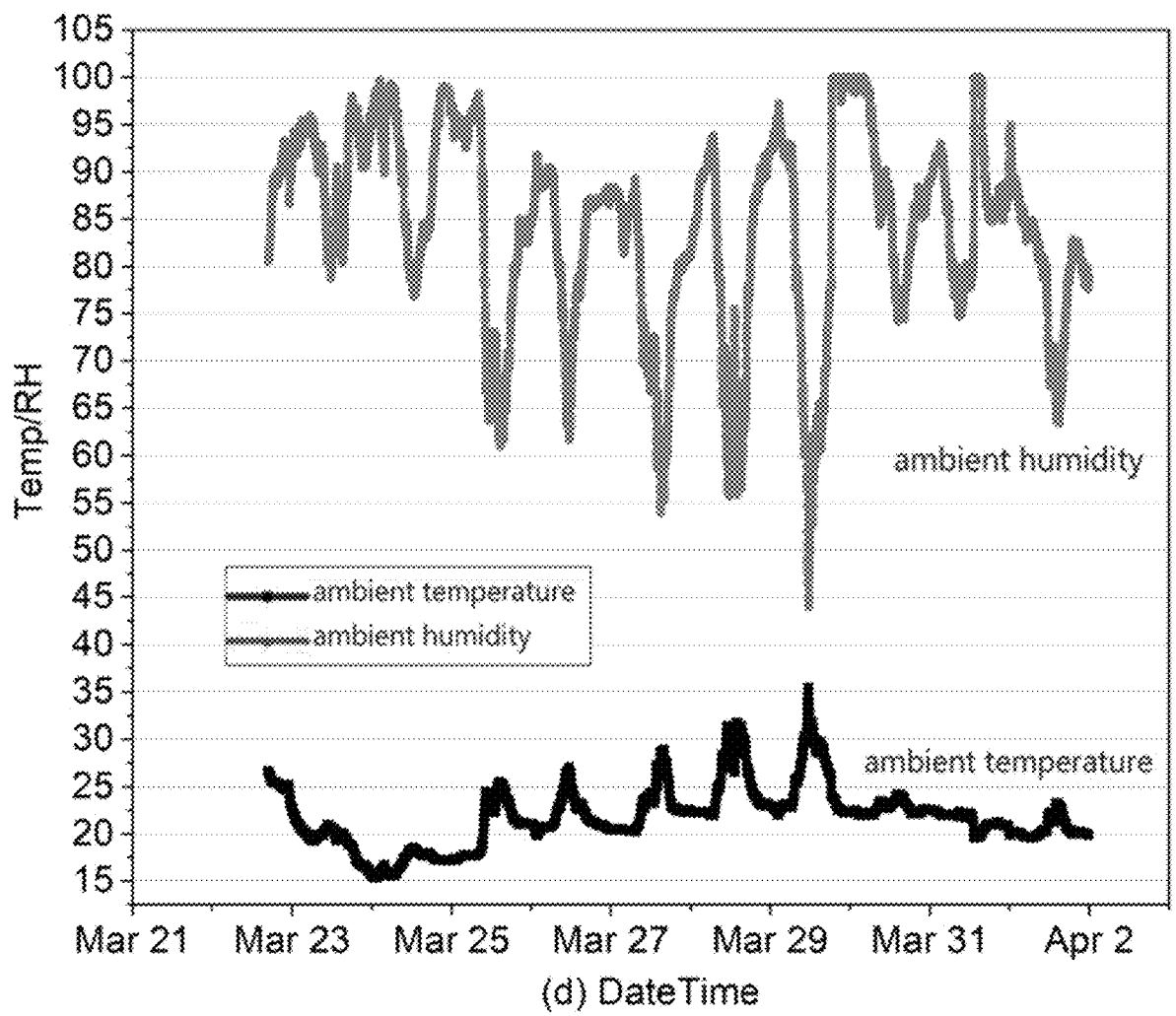

FIG. 4 is a schematic flowchart of the gas detection method with eliminating the influence of ambient temperature and humidity changes provided by the third embodiment of the present invention, which is applied to the gas detection system in first embodiment and second embodiment above. The method includes steps:

S1. Obtaining the first feedback signal by detecting a target gas in an ambient gas with a bare sensor 20;

S2. obtaining the second feedback signal by selectively isolating the target gas in the ambient gas to generate a zero gas and then detecting the zero gas with a reference sensor 30.

S3. calculating a difference value between the first feedback signal and the second feedback signal to obtain a third feedback signal, and obtaining a target gas concentration by calculating the third feedback signal according to a calibration formula.

Those skilled in the art can clearly understand that, for convenience and conciseness of description, the gas detection method may refer to the corresponding detection process in the gas detection system provided above, and the remaining implementation steps will not be repeated.

The following describes the implementation effect of the above gas detection system and its method through two specific embodiments:

In the first embodiment, the bare sensor 20 and the sensor body 31 selected are electrochemical nitrogen dioxide sensors that have a consistent reference shift signal response to ambient temperature and humidity changes, and the target gas selective isolation layer 32 selected can filter nitrogen dioxide gas and has the functions of heat conduction and water vapor exchange. The membrane of the target gas selective isolation layer 32 is covered on the reaction surface of the nitrogen dioxide sensor without gaps to form a reference sensor 30 (see FIG. 3 for details). The sampling gas path adopts active pumping sampling gas path.

Secondly, the bare nitrogen dioxide sensor and the reference nitrogen dioxide sensor are installed on the sensor seat and strictly sealed, and the nitrogen dioxide standard gas and temperature and humidity control device are used to produce a gas ambient with nitrogen dioxide concentration cyclic change in three gradients of 50 ppb-100 ppb-150 ppb, continuous change of ambient temperature between 15-40° C., and continuous change of ambient humidity between 15%-80%. During the experiment, it shall be recorded the voltage signal V1 of the bare nitrogen dioxide sensor and the voltage signal V2 of the reference nitrogen dioxide sensor, and then obtained the voltage signal V3 by calculating the direct difference, and calculated the target gas concentration according to the known standard gas change concentration and voltage signal V3.

FIGS. 5 (a), (b), (c) and (d) show the variation curve of the voltage signal V2 of the reference nitrogen dioxide sensor and the variation curve of the voltage signal V1 of the bare nitrogen dioxide sensor during sampling, The variation curve of temperature and humidity of standard gas, and the variation curve of target gas concentration finally obtained through difference calculation. It can be seen from the figure that the voltage signal V1 of the bare nitrogen dioxide sensor is affected by the gas temperature and humidity changes at the same time as the gas concentration changes. The reference nitrogen dioxide sensor removes the influence of the gas concentration. The voltage signal V2 fluctuates periodically with temperature and humidity, and the change range is large but the change is smooth. After signal processing, the target gas concentration by calculating the voltage signal V3 accurately reflects the change of the standard gas concentration in obvious preset gradients.

In the second embodiment, the gas detection system is basically the same as the first embodiment, and only change the packaging mode of the target gas selective isolation layer of the reference nitrogen dioxide sensor and the setting of the standard gas. The reference nitrogen dioxide sensor uses a non-close-fitting package, and a zero gas chamber is formed between the effective reaction surface of the sensor and the target gas selective isolation layer (see FIG. 2 for details). In addition, the nitrogen dioxide concentration fluctuates between 0 ppb-100 ppb, the gas temperature rises from −10 to 20° C. in a short period of time, and the humidity rises rapidly from 20% to 80%.

FIGS. 6 (a), (b), (c) and (d) respectively show the variation curve of the voltage signal V2 of the reference nitrogen dioxide sensor and the variation curve of the voltage signal V1 of the bare nitrogen dioxide sensor, the variation curve of temperature and humidity of standard gas, and the change curve of target gas concentration finally obtained through difference calculation during the sampling process. It can be seen from the figures that due to the rapid changes in gas temperature and humidity, the voltage signals of the reference nitrogen dioxide sensor and the bare nitrogen dioxide sensor both show fluctuation curves, but the variation curve of the target gas concentration calculated by the signal difference truly and accurately reflects that the standard gas concentration fluctuates between 0-100 ppb. From the above test results, it can be concluded that by using the dynamic sensor reference capturing technology provided by the present invention, the gas detection system finally effectively removes the influence of rapid environmental temperature and humidity changes on the sensor output signal.

FIGS. 7 (a), (b), (c) and (d) respectively show comparison curves between the concentrations of nitrogen dioxide, carbon monoxide and ozone pollutants obtained by using the gas detection system and method provided by the present invention and their standard concentrations respectively, and the corresponding ambient temperature and humidity variation curve. It can be seen from the figures that the accuracy of the sensor monitoring performance obtained by this method is close to it of the standard equipment method when the ambient relative humidity is within 45%-100% and the ambient temperature is within the range of 15-35° C., and the correlation coefficients of the hourly average value and the standard methods data are all above 0.95.

In summary, the present invention provides a gas detection system and method with eliminating the influence of ambient temperature and humidity changes, which comprising the steps as fellows: calculating the signal difference between the paired bare sensor and the reference sensor, obtaining the target gas concentration by calculating the signal difference. It effectively separates the target gas concentration signal and the ambient temperature and humidity signal from the sensor output signal, eliminates the effect of ambient temperature and humidity changes to the sensor output signal, and improves the accuracy, precision and ambient stability of the target gas concentration detection.

While the present invention has been described with reference to preferred embodiments, however, the present invention is not limited to above-mentioned embodiments, those modifications, improvements and equivalent substitutions, which don't depart from the scope of the spirit and the principle of the present invention, should be included within the scope of the present invention.

The invention claimed is:

1. A gas detection system with eliminating influence of ambient temperature and humidity changes, characterized in that the gas detection system comprising:
a bare sensor used to detect a target gas in an ambient gas to obtain a first feedback signal;
a reference sensor used to selectively isolate the target gas in the ambient gas to generate a zero gas, and to detect the zero gas to obtain a second feedback signal; and
a calculation module connected to the bare sensor and reference sensor being used to calculate a difference value between the first feedback signal and the second feedback signal to obtain a third feedback signal, and to obtain the target gas concentration by calculating the third feedback signal according to a calibration formula;
wherein the calibration formula is: $C = a*V3 + b$;
C is the target gas concentration, the unit of the target gas concentration is mass concentration or mixing ratio, V3 is the third feedback signal, the unit of the third feedback signal is consistent with output signal of the bare sensor and sensor body, and a and b are calibrated parameters.

2. The gas detection system according to claim 1, characterized in that the reference sensor comprises a sensor body having a consistent signal response to the target gas and ambient temperature and humidity with the bare sensor; and a target gas selective isolation layer having heat conduction and water vapor exchange function for selectively isolating the target gas in the ambient gas to generate the zero gas.

3. The gas detection system according to claim 2, characterized in that the gas detection system further comprises a sensor seat equipped with a sampling gas chamber communicated with the ambient gas, and the bare sensor and sensor body are installed in the sensor seat respectively.

4. The gas detection system according to claim 3, characterized in that the sensor seat is provided with a first accommodating cavity and a second accommodating cavity on both sides of the sampling gas chamber, a first sensor protective film is arranged between the sampling gas chamber and the first accommodating cavity, a second sensor protective film is arranged between the sampling gas chamber and the second accommodating cavity, the first accommodating cavity is used to install the bare sensor, and the second accommodating cavity is used to install the sensor body.

5. The gas detection system according to claim 4, wherein the target gas selective isolation layer is wrapped on one side of the second sensor protective film, and the side is facing the sampling gas chamber.

6. The gas detection system according to claim 5, wherein the number of sensor bodies is a plurality, and the plurality of sensor bodies are installed in the second accommodating cavity.

7. The gas detection system according to claim 4, wherein the target gas selective isolation layer is covered on reaction surface of the sensor body without gaps.

8. The gas detection system according to claim 3, wherein the gas detection system further comprises a sampling gas path connected the sensor seat, the sampling gas path includes a passive diffusion gas sampling gas path and an active pumping sampling gas path; wherein the active pumping sampling gas path includes an gas inlet pipe and an gas extraction pump, the gas inlet pipe is arranged on the sensor seat and communicated with the sampling gas chamber, and the gas extraction pump is communicated with the gas inlet pipe.

9. The gas detection system according to claim 2, wherein the gas detection system further comprises a first sensor seat and a second sensor seat, the first sensor seat and the second sensor seat are respectively equipped with a first sampling gas chamber and a second sampling gas chamber communicated with the ambient gas, the bare sensor is installed in the first sampling gas chamber, the sensor body is installed in the second sampling gas chamber.

10. The gas detection system according to claim 9, wherein the target gas selective isolation layer is covered on surface of the second sampling gas chamber.

11. The gas detection system according to claim 10, wherein the number of sensor bodies is a plurality, and the plurality of sensor bodies are installed in the second sampling gas chamber.

12. The gas detection system according to claim 9, wherein the target gas selective isolation layer is covered on reaction surface of the sensor body without gaps.

13. The gas detection system according to claim 2, wherein the bare sensor and sensor body comprise any one of electrochemical sensor, metal oxide sensor, photoionization sensor and non dispersive infrared sensor.

14. The gas detection system according to claim 2, wherein the target gas selective isolation layer includes any one of filter paper, filter membrane, molecular sieve, filter device and a coveting structures formed by selective filter material filling.

15. The gas detection system according to claim 2, wherein the sensor body is an electrochemical sensor, the target gas selective isolation layer is arranged on surface of internal electrolyte layer of the electrochemical sensor.

16. The gas detection system according to claim 1, characterized in that the first feedback signal, the second feedback signal and the third feedback signal include any one of voltage value, current value and concentration value.

17. The gas detection system according to claim 1, characterized in that the difference between the first feedback signal and the second feedback signal includes a direct signal difference between the first feedback signal and the second feedback signal and a correction signal difference after proportional correction between the first feedback signal and the second feedback signal.

18. A gas detection method with eliminating influence of ambient temperature and humidity change, applied to the gas detection system according to claim 1, the gas detection method comprising: obtaining a first feedback signal by detecting a target gas in an ambient gas with a bare sensor; obtaining a second feedback signal by selectively isolating the target gas in the ambient gas to generate a zero gas and detecting the zero gas with a reference sensor; and calculating a difference between the first feedback signal and the second feedback signal to obtain a third feedback signal, and obtaining a target gas concentration by calculating the third feedback signal according to a calibration formula.

19. A gas detection system with eliminating influence of ambient temperature and humidity changes, wherein the gas detection system comprising:

a bare sensor used to detect a target gas in an ambient gas to obtain a first feedback signal;

a reference sensor used to selectively isolate the target gas in the ambient gas to generate a zero gas, and to detect the zero gas to obtain a second feedback signal; and a calculation module connected to the bare sensor and reference sensor being used to calculate a difference value between the first feedback signal and the second feedback signal to obtain a third feedback signal, and to obtain the target gas concentration by calculating the third feedback signal according to a calibration formula;

wherein the reference sensor comprises a sensor body having a consistent signal response to the target gas and ambient temperature and humidity with the bare sensor; the gas detection system further comprises a sensor seat equipped with a sampling gas chamber communicated with the ambient gas, and the bare sensor and sensor body are installed in the sensor seat respectively.

20. A gas detection system with eliminating influence of ambient temperature and humidity changes, wherein the gas detection system comprising:

a bare sensor used to detect a target gas in an ambient gas to obtain a first feedback signal;

a reference sensor used to selectively isolate the target gas in the ambient gas to generate a zero gas, and to detect the zero gas to obtain a second feedback signal; and a calculation module connected to the bare sensor and reference sensor being used to calculate a difference value between the first feedback signal and the second feedback signal to obtain a third feedback signal, and to obtain the target gas concentration by calculating the third feedback signal according to a calibration formula;

the gas detection system further comprises a first sensor seat and a second sensor seat, the first sensor seat and the second sensor seat are respectively equipped with a first sampling gas chamber and a second sampling gas chamber communicated with the ambient gas, the bare sensor is installed in the first sampling gas chamber, the sensor body is installed in the second sampling gas chamber;

wherein the target gas selective isolation layer is covered on surface of the second sampling gas chamber.

* * * * *